United States Patent
Yewer, Jr.

(10) Patent No.: US 7,037,285 B2
(45) Date of Patent: May 2, 2006

(54) WRIST BRACE

(76) Inventor: Edward Henry Yewer, Jr., 6259 N. Highway 83, Hartland, WI (US) 53029

( * ) Notice: Subject to any disclaimer, the term of this patent is extended or adjusted under 35 U.S.C. 154(b) by 507 days.

(21) Appl. No.: 10/172,894

(22) Filed: Jun. 14, 2002

(65) Prior Publication Data
US 2002/0193719 A1 Dec. 19, 2002

Related U.S. Application Data

(60) Provisional application No. 60/298,472, filed on Jun. 15, 2001.

(51) Int. Cl.
A61F 5/00 (2006.01)
A61F 13/00 (2006.01)

(52) U.S. Cl. ........................................................ 602/21

(58) Field of Classification Search .................. 602/21, 602/19, 20, 5, 1, 61–64, 60; 2/16, 20; 128/877–880
See application file for complete search history.

(56) References Cited

U.S. PATENT DOCUMENTS

| 4,584,993 | A | * | 4/1986 | Nelson | 602/21 |
|---|---|---|---|---|---|
| 5,088,668 | A | | 2/1992 | Grimm | |
| 5,113,526 | A | * | 5/1992 | Wang et al. | 2/2.5 |
| D337,463 | S | | 7/1993 | Grimm | |
| 5,288,042 | A | | 2/1994 | Grimm | |
| 5,397,296 | A | | 3/1995 | Sydor | |
| 5,415,624 | A | * | 5/1995 | Williams | 602/21 |
| D360,467 | S | | 7/1995 | Sydor | |
| 5,484,392 | A | | 1/1996 | Sydor | |
| 5,538,501 | A | | 7/1996 | Caswell | |
| 5,557,806 | A | | 9/1996 | Caswell | |
| 5,632,045 | A | | 5/1997 | Chase | |
| D380,874 | S | | 7/1997 | Caswell | |
| D381,128 | S | | 7/1997 | Caswell | |
| 5,657,767 | A | | 8/1997 | Nelson | |
| 5,673,437 | A | | 10/1997 | Chase | |
| 5,695,453 | A | * | 12/1997 | Neal | 602/6 |
| D389,582 | S | | 1/1998 | Bodenschatz et al. | |
| 5,728,059 | A | * | 3/1998 | Wiesemann et al. | 602/64 |
| 5,759,166 | A | * | 6/1998 | Nelson et al. | 602/21 |
| 6,024,715 | A | * | 2/2000 | Maxwell | 602/64 |
| 6,063,048 | A | | 5/2000 | Bodenschatz | |
| 6,186,969 | B1 | * | 2/2001 | Bell et al. | 602/64 |
| 6,190,344 | B1 | * | 2/2001 | Bobroff | 602/21 |

OTHER PUBLICATIONS

DECADE Catalog of: Wrist/Arm Braces and Supports: Superior Products Made to Provide Relief From Pain and Injury. Chase Ergodynamics, Albuquerque, NM. No date given for publication.
Ergodyne Proflex Brochure: Wrist Supports, Ergodyne, St. Paul, MN, 1997.
Industrial Protective Gear Brochure: Back Support Systems, Tru-Fit, Lynn, MA, 1999.
Supports and Braces for Industrial and Safety Applications Catalog, Tamarack International, Chetek, WI. No publication date given.

* cited by examiner

Primary Examiner—Danton D. DeMille
Assistant Examiner—Huong Q. Pham
(74) Attorney, Agent, or Firm—Quarles & Brady LLP

(57) ABSTRACT

A sleeve-type wrist brace made of elastic material has a finger end and a forearm end, with an adjustable curved thumb strap and adjustable wrist straps.

1 Claim, 1 Drawing Sheet

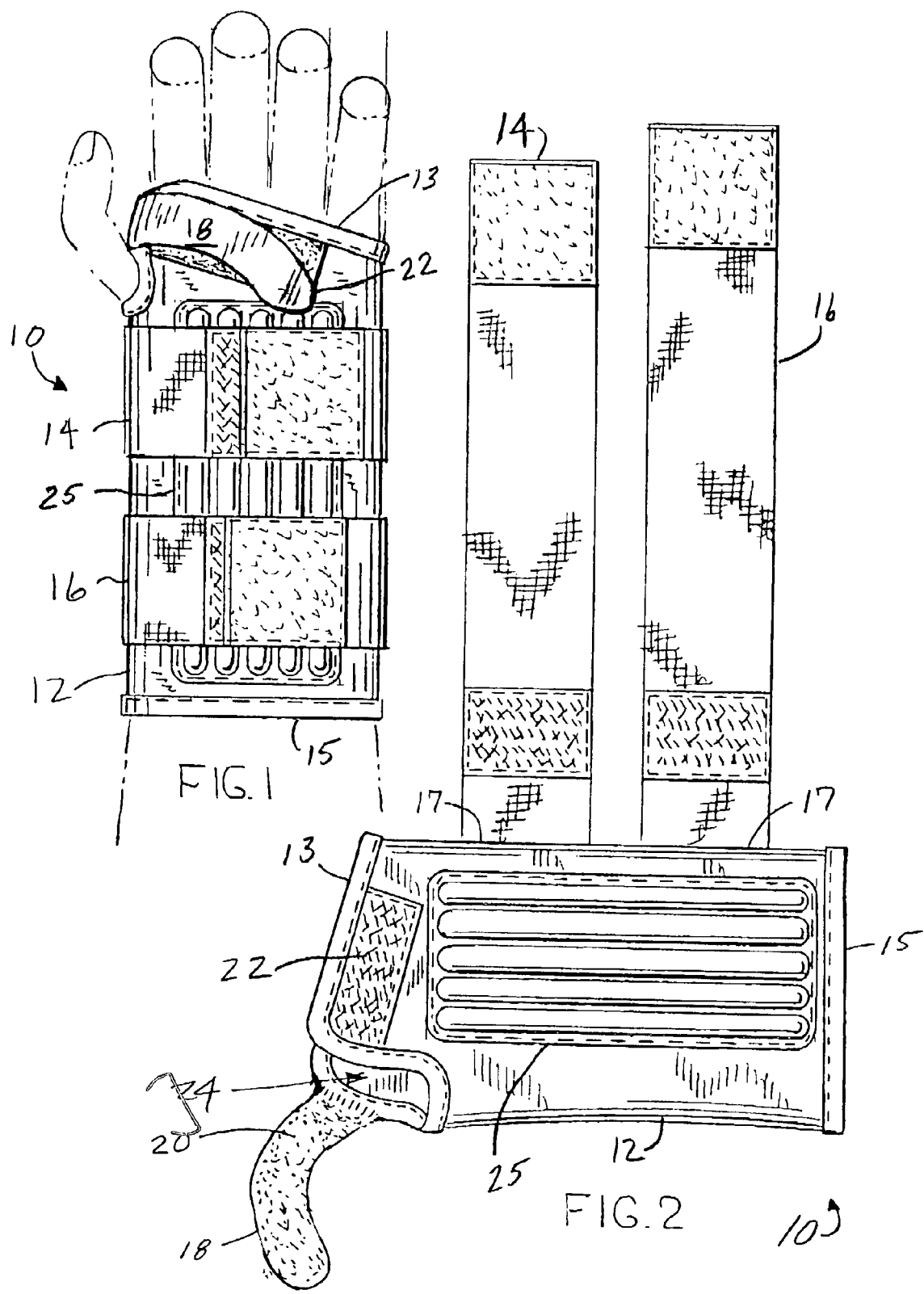

WRIST BRACE

CROSS-REFERENCE TO RELATED APPLICATION

This claims the benefit of U.S. Provisional Patent Application No. 60/298,472 filed, Jun. 15, 2001.

STATEMENT CONCERNING FEDERALLY SPONSORED RESEARCH OR DEVELOPMENT

Not applicable.

FIELD OF THE INVENTION

This invention relates to wrist braces of the type that are applicable to carpal tunnel syndrome or other wrist ailments.

BACKGROUND OF THE INVENTION

Wrist braces for treatment of carpal tunnel syndrome or other wrist ailments are well known and typically consist of an elastic wrap or an elastic tube which is pulled onto or wrapped around the wrist with some degree of tightness. Materials they are made of have included neoprene, which may be terry cloth covered, spandex, or other elastic materials. They may also be formed with stiffening batts running parallel to the user's arm to keep the arm and wrist area straight. The batts may be provided both on the front and the back of the wrist brace.

Such wrist braces have been made of the tubular type with a hole through the tube through which the thumb projects. These were made to be pulled on over the hand. Other braces have been made which are wrapped around the wrist with adjustable elastic wrap-around straps and an adjustable strap which is attached to one side of the brace by stitching or as an extension of the brace material itself, which is placed between the thumb and forefinger and attached to the other side of the brace with hook and loop type material. In prior art wrist braces, the adjustable thumb strap has typically been arranged so that it would first be connected to the hook and loop type material and then the elastic straps would be wrapped around the brace, over the adjustable thumb strap.

Tubular pull-on braces are preferred in some applications since they are easier to put on than wrap around braces. However, adjustment can be a problem with known pull-on braces, especially in the area of the thumb.

SUMMARY OF THE INVENTION

The present invention provides a tubular elastic wrist brace in which an adjustable thumb strap is provided which can be adjusted after straps of the brace are wrapped around and secured. A brace of the invention is ambidextrous, meaning it can be used on either hand with the adjustable thumb strap being attached over the back of the hand, for example, if it is used on the right hand, and being attached to the palm if it is used on the left hand. In either event, the straps which wrap around the brace do not cover the adjustable thumb strap and so it can be adjusted.

Preferably, in a wrist brace of the invention, the thumb strap is curved, so as to be concave on the side toward the thumb. This provides a better fit of the glove on the hand and more room to maneuver the thumb with the strap secured.

The foregoing and other advantages of the invention will appear in the detailed description which follows. In the description, reference is made to the accompanying drawings which illustrate a preferred embodiment of the invention.

BRIEF DESCRIPTION OF THE DRAWINGS

FIG. 1 is a view of the brace wrapped around a user's right hand looking at the back of the user's right hand; and FIG. 2 is a plan view of the brace showing all the straps laid out flat from the brace.

DETAILED DESCRIPTION OF THE PREFERRED EMBODIMENT

Referring to FIGS. 1 and 2, a brace 10 of the invention has a tubular main body 12 made of elastic material having a finger end 13 and a fore arm end 15. Elongated elastic straps 14 and 16 are stitched to the side of the body 12 at 17 opposite from U-shaped thumb slot 24 so as to be wrapped around the body 12 and attached to themselves with hook and loop material to secure them in the position of FIG. 1. An adjustable thumb strap 18 is made of an elastic material and stitched or integral with one edge of the thumb slot 24. The thumb strap 20 has its inner face provided with loop material 20, and is curved so as to be concave on the side adjacent to the thumb and convex on the opposite side. A patch of hook material 22, which may be either straight or curved, is stitched onto the body 12 immediately adjacent to the thumb slot 24 on the side of the slot 24 opposite from where the thumb strap 20 is attached to the sleeve 12 so that the loop material 20 can be adjustably affixed to the hook material 22.

As shown in FIG. 1, the thumb strap 18 is not overlapped by the wrap around strap 14 and so even after the strap 14 is secured, the adjustable strap 18 can be adjusted in between the thumb and forefinger to make it tighter or looser. In the position of FIG. 1, the fastener material 22 is over the back of the user's right hand and so the strap 18 is attached over the back of the user's hand. If the brace were applied to the user's left hand, the strap 18 and patch of material 22 would overlie the user's palm.

The body 12, being tubular, can be made of a single thickness of relatively breathable elastic material so that it is cooler to wear than many of the other types of wrap around wrist braces. The brace 10 also affords the advantage of having the adjustable thumb strap, even though it is a pull-on wrist brace.

Stiffening batting material 25 is preferably provided on both the palm side and the back hand side of the brace 10, with the thumb slot 24 between the two areas of batting 25.

A preferred embodiment of the invention has been described in considerable detail. Many modifications and variations to the embodiment described will be apparent to those skilled in the art. Therefore, the invention should not be limited to the embodiment described, but should be defined by the claims which follow.

I claim:

1. An elastic wrist brace, comprising:
a sleeve of flexible material, said sleeve being a tubular structure that is closed around its circumference when not worn by a human and having two opposite open ends, one end being a finger end and the other end being a forearm end, said finger end including a thumb slot which has an open end and a closed end, with the open end at the finger end of the sleeve, said slot extending in the direction from the finger end of the sleeve toward the forearm end of the sleeve;

a thumb strap attached to said sleeve at one side of said thumb slot and extending therefrom so as to be planed in a position to bridge the open end of said thumb slot and extend onto a palm side of said sleeve;

said thumb strap having two longitudinal edges, the edge adjacent the thumb is concave and the opposite edge is convex;

fastener material on an inside surface of said thumb strap and on an outer surface of said sleeve adjacent to said thumb slot opposite from said thumb strap on said palm side of said sleeve so that said thumb strap can be attached to said material adjacent to said thumb slot on said palm side of said sleeve;

a strap having one end affixed to said sleeve between said finger end and said forearm end, said strap being adapted to be wrapped around said sleeve in a circumferential direction so as not to overlie said thumb strap when said thumb strap is secured to said fastener material adjacent said thumb slot on said palm side of said sleeve; and wherein a longitudinally extending axis of symmetry of said thumb strap and said fastener material on said thumb strap is curved where said thumb strap and fastener material on said thumb strap overlies said fastener material on said palm side of said sleeve.

* * * * *

UNITED STATES PATENT AND TRADEMARK OFFICE
CERTIFICATE OF CORRECTION

| | | |
|---|---|---|
| PATENT NO. | : 7,037,285 B2 | Page 1 of 1 |
| APPLICATION NO. | : 10/172894 | |
| DATED | : May 2, 2006 | |
| INVENTOR(S) | : Edward H. Yewer, Jr. | |

It is certified that error appears in the above-identified patent and that said Letters Patent is hereby corrected as shown below:

Col. 3, line 6, Claim 1, "planed" should be --placed--.

Signed and Sealed this

Twenty-first Day of November, 2006

JON W. DUDAS
*Director of the United States Patent and Trademark Office*